United States Patent [19]

Goldberg

[11] 4,353,822

[45] Oct. 12, 1982

[54] ANTIGENIC LINEAR PEPTIDE COMPOUNDS

[75] Inventor: Erwin Goldberg, Evanston, Ill.

[73] Assignee: Northwestern University, Evanston, Ill.

[21] Appl. No.: 267,021

[22] Filed: May 26, 1981

[51] Int. Cl.$^3$ .......................................... C07C 103/52
[52] U.S. Cl. ............................................. 260/112.5 R
[58] Field of Search ................................. 260/112.5 R

[56] References Cited

U.S. PATENT DOCUMENTS 4,310,456  1/1982  Goldberg ..................... 260/112.5 R

OTHER PUBLICATIONS

Chem. Abstr. vol. 95, (1981) pp. 128346w, vol. 78, (1973) pp. 41298g.
Musick, et al., J. Biol. Chem. 254, 1979, 7621–7623.

*Primary Examiner*—Delbert R. Phillips

[57] ABSTRACT

The novel antigenic linear peptide compounds of this invention are characterized by providing a sequence of eight amino acids comprising isoleucine-serine-glycine-phenylalanine-proline-valine-glycine-arginine, all of the amino acids with the exception of glycine being in their L-forms. The isoleucine may comprise the N-terminal end or may be bonded to N-terminal glycine, and the arginine may be the C-terminal amino acid or may be bonded to C-terminal valine. The compounds have utility in vaccines for reducing the fertility of mammals.

5 Claims, No Drawings

ANTIGENIC LINEAR PEPTIDE COMPOUNDS

BACKGROUND AND PRIOR ART

Mammalian spermatozoa have been known to be antigenic for many years. More recently, it has been demonstrated that mammalian sperm contain an antigenic enzyme, which is known as the $C_4$ isozyme of lactate dehydrogenase (LDH-X, LDH-$C_4$). LDH-$C_4$ has been isolated in pure crystalline form from mouse testes. Goldberg (1972) *J. Biol. Chem.* 247:2044–2048. The enzyme has a molecular weight of 140,000 and is composed of four identical C subunits. The amino acid sequence and three-dimensional structure of LDH-$C_4$ has been studied and partially determined by a number of investigators. See Musick et al (1976) *J. Mol. Biol.* 104:659–668; and Wheat et al (1977) *Biochem. & Biophys. Res. Comm.*, 74, No. 3:1066–1077. Wheat et al determined the sequence of the essential thiol peptide from amino acid 159 to 171, and found this to be nearly identical to essential thiol peptides from other vertebrate LDH isozymes.

In 1974, Dr. Erwin Goldberg reviewed the effects of immunization with LDH-X (LDH-$C_4$) on fertility, and advanced the possibility that "by using a defined macromolecular constituent of sperm it becomes possible to elucidate its primary structure in terms of amino acid sequence, to map specifically the antigenic determinant(s) responsible for inducing infertility, and then to construct synthetic peptides containing these determinants. Possessing the capability for synthesizing a molecule with such properties, makes the immunological approach to fertility control feasible." Karolinska Symposia on Research Methods in Reproductive Endocrinology, 7th Symposia: Immunological Approaches to Fertility Control, Geneva, 1974 202–222. However, such synthetic antigenic peptide remained a goal and not an achievement, although their theoretical desirability had been recognized. In 1979, Dr. Erwin Goldberg summarized the state of the art as follows:

"In conclusion, and on a practical basis, immunotherapy for birth control requires more than effectiveness, specificity, reversibility, and absence of systemic side reaction. Rather large amounts of the antigen must be available in unequivocally pure form. This condition probably cannot be met by a natural product enzyme antigen from sperm or testes. Rather, contraceptive technology requires a synthesizable peptide fragment retaining antigenicity and provoking a response which impairs fertility. Completion of the structural analysis of LDH-$C_4$ should allow mapping of antigenic determinants and synthesis of such peptides for use in a new contraceptive technology." *"Recent Advances in Reproduction and Regulation of Fertility,"* G. P. Talwar, editor, Elseview/North Holland Biomedical Press (1979).

SUMMARY OF INVENTION

It has now been discovered that a highly antigenic peptide can be prepared by synthesizing a linear sequence of eight amino acids comprising: isoleucine-serine-glycine-phenylalanine-proline-valine-glycine-arginine. All of the amino acids used to prepare the foregoing peptide are in their L-form with the exception of glycine. The isoleucine is at the N-terminal and arginine is at the C-terminal. The antigenic action of the peptide can be enhanced by the addition of glycine to the N-terminal isoleucine, and/or the addition of valine to the C-terminal arginine. Thus, the antigenic linear peptide compounds of the present invention include at least four compounds having chain lengths of from eight to ten amino acids, all of which include the eight amino acid sequence from isoleucine to arginine, and have as a N-terminal either isoleucine or glycine, and as the C-terminal either arginine or valine. From a recent publication, it can be seen that the primary antigenic sequence of eight amino acids from isoleucine to arginine corresponds with amino acids 152 to 159 of LDH-$C_4$, while lycine is amino acid 151 and valine amino acid 160. Musick et al (August 25, 1979), *J. Biol. Chem.*, 254, No. 16:7621–7623.

DESCRIPTION OF INVENTION

The present invention relates to a novel class of antigenic linear peptides having chain lengths of from eight to ten amino acids and which are characterized by containing a specific antigenic sequence. Four compounds coming within the class of compounds of this invention are identified as follows:

(1) N-Ile-Ser-Gly-Phe-Pro-Val-Gly-Arg-C (2) N-Ile-Ser-Gly-Phe-Pro-Val-Gly-Arg-Val-C (3) N-Gly-Ile-Ser-Gly-Phe-Pro-Val-Gly-Arg-C (4) N-Gly-Ile-Ser-Gly-Phe-Pro-Val-Gly-Arg-Val-C

In the foregoing formulas, the letter "N" designates the N-terminal amino acid, while the letter "C" designates the C-terminal amino acid. Gly represents glycine, and Ile, Ser, Phe, Pro, Val, and Arg respectively represent the L-amino acid forms of isoleucine, serine, phenylalanine, proline, valine, and arginine. As will be noted, all of the compounds include the amino acid sequence of compound (1). In compound (2), valine is added at the C-terminal end to act as a spacer amino acid and thereby enhance immunogenicity. This will move the antigenic binding site further from the free carboxyl group. Alternatively, glycine may be added to the N-terminal end to serve as a spacer for improving immunogenicity, as represented by compound (3). Other amino acids can similarly be used as spacers at the terminal ends of the basic antigenic sequence (1). The preferred antigenic compound is therefore compound (4), which contains ten amino acids with N-terminal glycine and C-terminal valine. As will be apparent to those skilled in the art of immunology, other C- and N-terminal amino acids can be substituted while retaining or enhancing antigenicity.

In studies leading to the discovery of the foregoing peptide compounds, pure crystalline lactate dehydrogenase-$C_4$ was digested with trypsin in 2 molar urea at 37° C. for 4 hours to produce a mixture of peptide fragments. This mixture was subjected to chromatography on a strong cation exchanger. The adsorbed peptide fragments were eluted at 50° C. with a gradient from 0.01 M pyridine-acetate, pH 3.1 to 2.0 M pyridine-acetate, pH 5.0. The eluted peptides were detected with fluorescamine. The eluates from the column provided eleven mixtures of peptides. An assay was developed for determining antibody binding of the peptide fragments. In an adaptation of a solid matrix radioimmunoassay, an aqueous solution of the peptides is used to coat the surface of the wells of a polyvinylchloride microtiter plate. The plate is then reacted with anti-LDH-C$_4$ such that the bound peptides complex with specific antibody. The amount of bound antibody is then quantitated with a labelled second antibody. This provides a measure of the extent of the interaction between a particular peptide or mixture of peptides and antibody to native LDH-C$_4$. The eleven mixtures of peptides were tested by this procedure. Only one fraction was found to be active, which was also shown to be a single peptide. All of the other fractions were either inactive or were a mixture of peptides. The isolated antigenically active peptide thus discovered was found to correspond in structure to compound (1) as set out above. This peptide at a concentration of $1.5 \times 10^{-4}$ M binds 1309 cpm of anti-LDH-C$_4$ but only 96 cpm of control gamma globulin.

The peptide compounds of the present invention can be synthesized from their constituent amino acids. For example, the synthesis can be carried out by the Merrifield solid phase method, as described in *J.A.C.S.* 85:2149–2154 (1963). This solid phase method for synthesizing sequences of amino acids is also described in Stewart and Young, *Solid Phase Peptide Synthesis* (W. H. Freeman and Co., San Francisco, 1969), pages 1–4. In this procedure, the C-terminal amino acid, such as arginine for compounds (1) and (3) or valine for compounds (2) and (4), is attached to chloromethylated polystyrene-divinylbenzene copolymer beads. Each subsequent amino acid, with suitable protecting group, is then added sequentially to the growing chain. For example, as described in the Merrifield article, the protective group may be a carbobenzoxy group. By the procedure of coupling, deprotection, and coupling of the next amino acid, the desired amino acid sequence and chain length can be produced. As a final step, the protective group is removed from the N-terminal amino acid, and the C-terminal amino acid is cleaved from the resin, using a suitable reagent, such as trifluoroacetic acid and hydrogen bromide. Since this synthesis procedure is well known, it is not believed that it will be necessary to further describe it herein. Compounds (1), (2), (3), and (4), as described above, are prepared by this synthesis procedure for use in reducing the fertility of mammals.

To utilize an antigenic peptide of this invention in the form of a fertility reducing vaccine, the peptide is conjugated to a carrier molecule, which is preferably a protein which itself elicits an antigenic response and which can be safely administered. For example, the peptide can be coupled to tetanus toxoid for administration by intramuscular injection. For example, a mixture of 1μ Mole tetanus toxoid, 60μ Moles antigenic peptide, and 18 millimoles 1-ethyl-3-(3 dimethyl aminopropyl) carbodiimide hydrochloride reacted in water (pH 6) for 12 hours at room temperature and 24 hrs. at 4° gives a product containing 3.5 moles of peptide/mole of tetanus toxoid. Excess reactants can be removed by dialysis or gel filtration. See Pique et al, *Immunochemistry*, 15:55–60 (1978). Alternatively, the peptide may be coupled using bisdiazotized benzidine [Bassiri et al, *Endocrinology*, 90:722 (1972)] or glutaraldehyde.

For intramuscular injection, the coupled peptide may be suspended in a sterile isotonic saline solution, or other conventional vehicle, and, if desired, an adjuvant may be included. A preferred use of such a vaccine is for administration to human females. Antibodies will be formed, which will appear in the oviduct fluids and thereby achieve a significant reduction in fertility. For this purpose, the amount to be administered will range from about 1 to 10 milligrams (mg) of the antigenic peptide.

I claim:

1. The linear peptide compounds having chain lengths of from 8 to 10 amino acids arranged in a sequence from N-terminal to C-terminal amino acids which include the antigenic sequence Ile-Ser-Gly-Phe-Pro-Val-Gly-Arg, said compounds being selected from the class of compounds consisting of:

(a) Ile-Ser-Gly-Phe-Pro-Val-Gly-Arg, (b) Ile-Ser-Gly-Phe-Pro-Val-Gly-Arg-Val, (c) Gly-Ile-Ser-Gly-Phe-Pro-Val-Gly-Arg, and (d) Gly-Ile-Ser-Gly-Phe-Pro-Val-Gly-Arg-Val, wherein Gly represents glycine, and Ile, Ser, Phe, Pro, Val, and Arg, respectively represent the L-amino acid forms of isoleucine, serine, phenylanine, proline, valine, and arginine.

2. The antigenic peptide of claim 1 having the amino acid sequence (a).

3. The antigenic peptide of claim 1 having the amino acid sequence (b).

4. The antigenic peptide of claim 1 having the amino acid sequence (c).

5. The antigenic peptide of claim 1 having the amino acid sequence (d).

UNITED STATES PATENT OFFICE
CERTIFICATE OF CORRECTION

Patent No. 4,353,822　　　　　　　　　　Dated October 12, 1982

Inventor(s) Erwin Goldberg

It is certified that error appears in the above-identified patent and that said Letters Patent are hereby corrected as shown below:

In column 1 of the patent following the title insert the following notice: -This invention was developed in part under Grant HD 05863 by The National Institutes of Health.-

Signed and Sealed this

Twelfth Day of June 1984

[SEAL]

*Attest:*

GERALD J. MOSSINGHOFF

*Attesting Officer*　　　*Commissioner of Patents and Trademarks*